US008945593B2

United States Patent
LoCoco et al.

(10) Patent No.: US 8,945,593 B2
(45) Date of Patent: Feb. 3, 2015

(54) ORALLY INGESTED METABOLIC ENHANCER IN ORAL THIN FILM CONTAINER

(76) Inventors: Tony LoCoco, Siesta Key, FL (US); Robert LoCoco, Orland Park, IL (US); Priscilla LoCoco, Plainfield, IL (US)

(*) Notice: Subject to any disclaimer, the term of this patent is extended or adjusted under 35 U.S.C. 154(b) by 118 days.

(21) Appl. No.: 13/565,903

(22) Filed: Aug. 3, 2012

(65) Prior Publication Data
US 2013/0039955 A1 Feb. 14, 2013

Related U.S. Application Data

(60) Provisional application No. 61/522,027, filed on Aug. 10, 2011.

(51) Int. Cl.
*A61K 9/00* (2006.01)
*A61P 3/00* (2006.01)
*A24F 47/00* (2006.01)
*A61K 31/522* (2006.01)
*A61K 9/70* (2006.01)
*A23L 1/00* (2006.01)

(52) U.S. Cl.
CPC ............ *A23L 1/0067* (2013.01); *A23V 2002/00* (2013.01)
USPC ........... 424/400; 131/352; 131/347; 131/270; 424/443; 514/263.31

(58) Field of Classification Search
USPC .............. 424/400, 443; 514/263.31; 131/352, 131/347, 270
See application file for complete search history.

(56) References Cited

U.S. PATENT DOCUMENTS

| | | | |
|---|---|---|---|
| 2003/0185881 A1* | 10/2003 | Nowak | 424/463 |
| 2005/0241658 A1* | 11/2005 | Pera | 131/352 |
| 2007/0031539 A1 | 2/2007 | Calton | |
| 2007/0062549 A1* | 3/2007 | Holton et al. | 131/352 |
| 2008/0260807 A1* | 10/2008 | Sharp et al. | 424/443 |
| 2009/0022917 A1* | 1/2009 | Gedevanishvili et al. | 428/35.2 |

OTHER PUBLICATIONS

Dipping tobacco: retrieved from internet: http://en.wikipedia.org/wiki/Dipping_tobacco. Retrieved on Jan. 14, 2014.*
Buerki: Dosage forms and basic preparations: history, Encyclopedia of Pharmaceutical technology, 2007, by Informa Healthcare USA, Inc.*
Caffeine & Nicotine: retrieved from internet: http://www.livestrong.com/article/91383-caffeine-nicotine/. Retrieved on May 23, 2014.*
Hour glass shape on the pill: retrieved from internet: http://www.medschat.com/topics/hour-glass-shape-on-the-pill/. Retrieved on May 23, 2014.*
http://www.sheetsbrand.com/#energy-page (published 2012).

* cited by examiner

*Primary Examiner* — Ernst V Arnold
*Assistant Examiner* — Hong Yu
(74) *Attorney, Agent, or Firm* — Daniel Boudwin; Global Intellectual Property Agency LLC

(57) ABSTRACT

An orally ingestible energy-boosting device is provided for facilitating a temporary metabolic increase in a user. The device comprises a small container filled with an energy-enhancing substance. All or a portion of the small container is constructed of a water or saliva-soluble film that dissolves when placed in the mouth of a user. When the film dissolves, energy-enhancing substance is released into the mouth where it is absorbed. The small container may come in a variety of shapes and configurations to meet the varied energy boost needs of users.

6 Claims, 2 Drawing Sheets

ORALLY INGESTED METABOLIC ENHANCER IN ORAL THIN FILM CONTAINER

CROSS-REFERENCE TO RELATED APPLICATION

This application claims the benefit of U.S. Provisional Application No. 61/522,027 filed on Aug. 10, 2011, entitled "Beans in a Bag or Energy Squared."

BACKGROUND OF THE INVENTION

1. Field of the Invention

The present invention relates to a capsule filled with an energy-enhancing substance. A portion of the capsule is constructed of a water or saliva-soluble material, so that it dissolves when placed in a user's mouth, releasing the energy-enhancing substance for consumption. The invention will be appreciated by busy users who lack the time to drink a caffeinated beverage as well as those users performing activities that require both hands, rendering it difficult to continuously pick-up and drink from a beverage.

Every day individuals struggle with the symptoms of fatigue. It manifests in several forms including mental, physical and even emotional fatigue. The symptoms of mental sluggishness, weary muscles, and lack of energy can make it difficult for a person to make it through their workday. Tasks requiring mental acuity, attention to detail, and precision motor skills can be excruciatingly difficult under the effects of fatigue. To combat these effects people often consume caffeinated beverages such as coffee, tea or energy drinks. Consumption of energy-enhancing beverages can be problematic if a vendor is not readily available or if a user's work requires both hands. For instance doctors and nurses may be unable to leave an emergency area to procure a caffeinated beverage, or may not be allowed to have a beverage container within a sterile area. A solution is needed that provides individuals with an energy-enhancing substance in a form that does not require messy beverages or the use of a person's hands.

2. Description of the Prior Art

Oral energy supplements are ingested by a user to obtain a temporary increase in overall body energy. A variety of substances are used to provide different effects to a user. The present invention is an oral energy supplement with the structure of a capsule containing an energy enhancing substance. Any portion of the capsule can be water or saliva-soluble. The prior art fails to describe a capsule containing an energy-enhancing substance, that is constructed wholly or in part, of a water or saliva-soluble material.

Calton, U.S. Patent Application Publication No. 2007/0031539 discloses a saliva-permeable pouch containing a caffeinated substance. The pouch is elongated and sealed at either end to create an interior pocket region. Coffee grounds, tea or other caffeinated substances may be stored within the interior pouch. When the pouch is placed within a user's mouth, saliva enters the interior pocket through small perforations in the walls of the pouch. Saliva activates the caffeinated substances, which then flows back across the walls of the pouch and into a user's mouth for digestion. The device of Calton is made of a saliva-permeable material such as cloth or plastic mesh. Saliva is allowed to enter and exit the interior pocket, but the walls of the device do not breakdown and dissolve. This means that a user must hold the pouch in his or her mouth for an extended period of time while caffeine is released. The pouch must then be removed from the user's mouth and discarded in a trash receptacle. This may be problematic for users who must talk often or those who are uncomfortable with leaving foreign objects in their mouths. The present invention solves this problem by providing a capsule that dissolves in a user's mouth, releasing the energy-enhancing substance into the mouth of a user. Thus there is no need for the user to hold the pouch in his or her mouth for an extended period. Users ingest larger amounts of the energy-enhancing substance than they would if the device were only saliva-permeable, resulting in a stronger boost of energy.

Another energy-boosting device is disclosed by "Sheets Brand™". The device comprises a thin film that is water-soluble and contains a variety of pharmaceutical agents that activate when the film dissolves. Pharmaceutical agents may include chemicals for providing energy enhancement or facilitate sleep. The user takes a sheet of the film, places it on the tongue and then closes his or her mouth to flood the area with saliva. As the film breaks down, pharmaceutical agents are released into the flow of saliva and absorbed into the tongue. In this way, an energy booster or sleep aid is delivered to the user quickly. The device does not comprise an encapsulated area or enclosed space. It does not contain a particulate form of an energy-enhancing substance. The present invention provides a capsule that is wholly or partially dissolvable and contains an energy-enhancing substance. Because the substance is released into the mouth and digested, energy-enhancement is experienced in stages. First as the initial product is released into the mouth, then as the substance is digested. The present invention thus provides a longer lasting energy boost.

Sometimes referred to as oral thin films (OTFs), the rapidly dissolving water-soluble materials are used as an alternative to conventional pills and tablets. Active pharmaceutical ingredients (APIs) can be included in the film material during construction, and released into a user's mouth upon contact with saliva. Though the films are often used to facilitate the transfer of medicines to children, or breath fresheners to adults, the prior art does not disclose their use as dissolvable containers for energy-enhancing substances. The present invention uses small containers constructed in whole or in part of oral thin films to hold a substance while it is being absorbed by the human mouth.

The present invention provides a capsule that contains an energy-enhancing substance and is wholly or partially saliva-soluble. The prior art fails to disclose a device having the structure of the present invention and further fails to provide the same benefits as the present invention. It substantially diverges in design elements from the prior art and consequently it is clear that there is a need in the art for an improvement to existing orally ingested energy-boosting devices. In this regard the instant invention substantially fulfills these needs.

SUMMARY OF THE INVENTION

In view of the foregoing disadvantages inherent in the known types of orally ingested energy boost devices now present in the prior art, the present invention provides a new saliva-soluble capsule wherein the same can be utilized for providing convenience for the user when a user desires temporary improved energy while on the go.

The invention comprises a small container such as a capsule, pill sheath, or pouch. The container is sized to fit in a person's mouth so that a user may comfortably manipulate the device with his or her tongue. A water or saliva-soluble material is used to construct a portion of, or the entire small container. Thus, when the container is placed in the mouth of a user it begins to break down upon contact with the user's saliva.

Enclosed within the small container is an energy-enhancing substance such as caffeinated powders, coffee, tea, or chemical compounds designed to illicit physiological responses associated with heightened awareness. As the small container dissolves in a user's mouth, the substance is released. Saliva will activate the substance, causing it to release stimulant for absorption by the soft tissues of a user's mouth. Some of the substance will be swallowed and digested, creating a second release of stimulant. The device will be appreciated by users requiring immediate energy enhancement as well as prolonged energy boosts.

It is therefore an object of the present invention to provide a new and improved orally ingested energy boosting device that has all of the advantages of the prior art and none of the disadvantages.

It is another object of the present invention to provide a small container filled with energy-enhancing substance that is safe for human consumption.

Another object of the present invention is to provide a water or saliva-soluble container to facilitate the release of an energy-enhancing substance into the mouth of a user.

Yet another object of the present invention is to provide an orally ingestible energy source that does not require a user to continuously hold a beverage cup or other object.

Still another object of the present invention is to provide a temporary but continuous boost of energy to a user.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
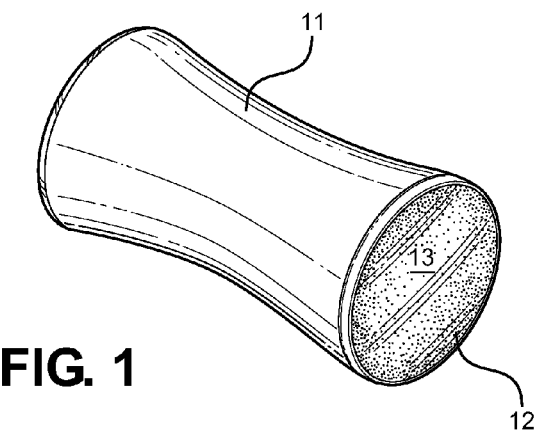
FIG. 1 shows a perspective view of the orally ingested energy-boosting device in a capsule container.

Reference is made herein to the attached drawings. Like reference numerals are used throughout the drawings to depict like or similar elements of the orally ingested energy-boosting device. For the purposes of presenting a brief and clear description of the present invention, the preferred embodiment will be discussed as used for providing temporary energy boosts to a user. The figures are intended for representative purposes only and should not be considered to be limiting in any respect.

Referring now to FIG. 1, there is shown a perspective view of the capsule embodiment of the present invention. The device comprises a small container 11 having an outer shell defining an interior cavity space. In the capsule embodiment the small container has a first and second end that may be part of the container or may be constructed of a water or saliva-soluble film. An energy-enhancing substance 12 is enclosed within said interior cavity of the container. The small container has an hourglass shape to conform to the convex curvature of a person's lips. The container can be placed between the lips and held in place while the user gently sucks on the interior portion of the device. One or both ends of the small container are sealed with a water or saliva-soluble film 13 (oral thin film). This film begins to breakdown upon contact with the user's saliva. The energy-enhancing substance is then released into the user's mouth for absorption. In a preferred embodiment the capsule is made of a non-water or saliva-soluble material that is safe for human consumption. This construction allows the small container to be removed from the user's mouth or swallowed according to the preference of the user. In an alternative embodiment the small container is constructed of water or saliva-soluble material so that the entire container breaks down upon entering a user's mouth.

Figure 2:
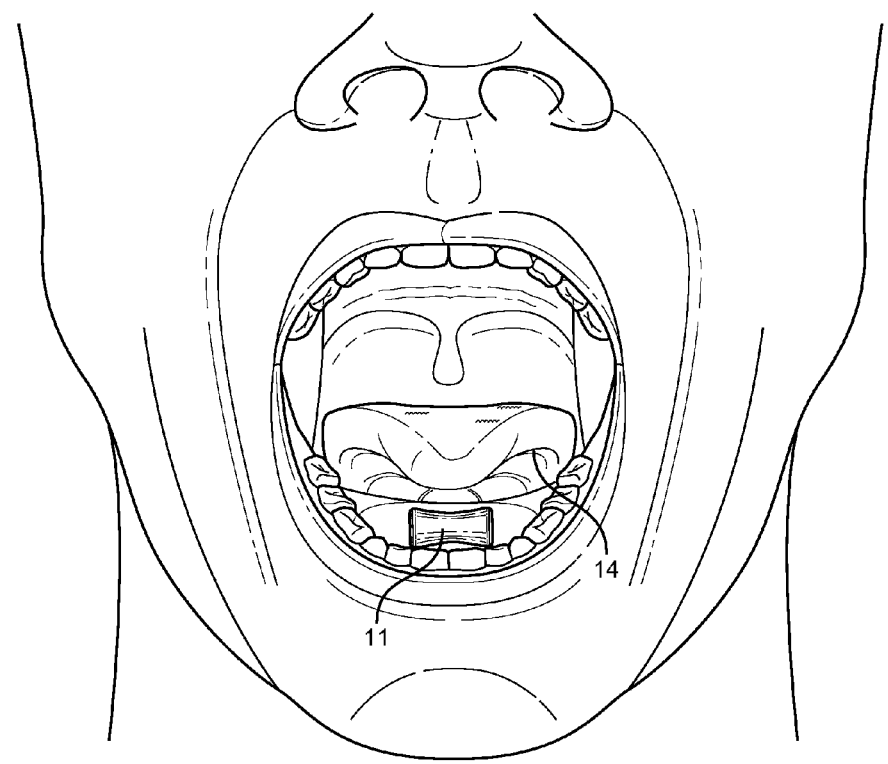
FIG. 2 shows a perspective view of a user's open mouth with the device lying between the user's tongue and the sidewall of the mouth.

Referring now to FIG. 2, there is shown a perspective view of a user's open mouth with the device positioned near the tongue 14. The small container 11 is held in the mouth by the tongue while the film dissolves. The container may be held in any desired position within the mouth and manipulated as needed by the user to withdraw the energy-enhancing substance from the container. If the small container is constructed of a non-saliva soluble material then the container is removed from the mouth after use. Alternatively, the container may dissolve in the mouth completely, allowing for absorption of all of the energy-enhancing substance.

Figure 3:
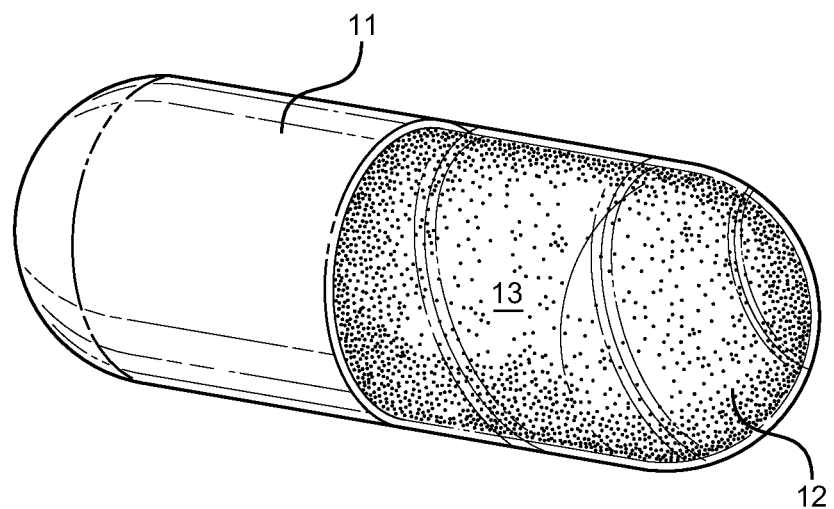
FIG. 3 shows a perspective view of the pill sheath embodiment of the device.
Figure 4:
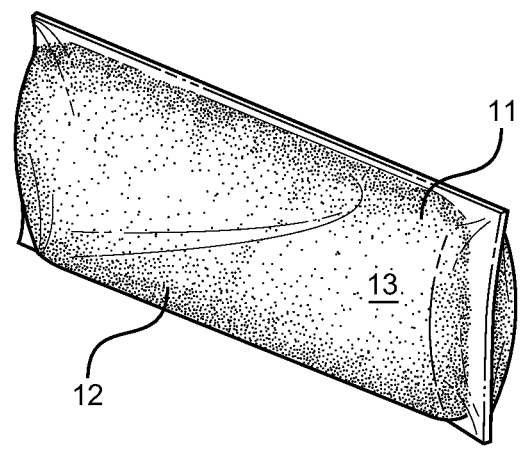
FIG. 4 shows a perspective view of the pouch embodiment of the present invention.

An alternative embodiment of the small container is shown in FIG. 3 as a pill sheath filled with an energy-enhancing substance 12. The small container 11 comprises a first and second half wherein at least one half is constructed of the water or saliva-soluble film 13. Both halves may be made of the film to provide a more even distribution of the energy-enhancing substance into a user's mouth as the small container dissolves. Another alternate embodiment is shown in FIG. 4, where the small container 11 is a pouch. The pouch is constructed entirely of the water or saliva-soluble film 13 and encloses the energy-enhancing substance 12. This embodiment can hold larger quantities of the energy-enhancing substance and therefore will be appreciated by users who require a more significant energy boost.

In use an individual places the small container in his or her mouth and gently sucks on the device. As the user's saliva comes into contact with the portions of the device constructed from saliva-soluble film, the film begins to dissolve. Energy-enhancing substance is released into the mouth of the user where it interacts with saliva. A portion of the substance is absorbed into the tissue of a user's mouth, entering the blood stream and initiating a physiological response. Unabsorbed quantities of the substance are swallowed by the user. The swallowed portions are absorbed as they traverse the user's digestive tract resulting in continuous physiological response. Responses may include, but are not limited to, temporarily 1) improved mental function, 2) enhanced metabolism and metabolic function, as well as 3) improved performance of physical activities and 4) increased physical endurance.

Construction of the small container may be made wholly or in part from a rapidly dissolving water or saliva-soluble film. Oral thin films are well known in the art of pharmaceuticals and are made from a variety of materials. One of ordinary skill in the art will be able to identify the type of film best suited to containing different types of energy-enhancing substances.

Thus the type of film used in the product may vary according to the type of energy-enhancing substance enclosed in the small container. Portions of the small container that are not constructed of oral thin film may be made from plastic, which is removed from the mouth after use, or any slowly dissolving coating, that can be digested by a user's system after swallowing.

The type and quantity of energy enhancing substance will vary in production to meet the needs of different users. Powdered coffee, tea, or other stimulants may be used. Vitamins such as C, B3, B12, E, A, B6 and others can be combined with minerals and extracts such as Ginkgo Biloba, Ginger, Ginseng, Niacin, Thiamine, Taurine and others, to create a metabolic enhancer that provides short term energy boosts to a user. Natural and artificial flavors may be added to give the energy—enhancing substance a pleasant taste. Any energy-enhancing substance that is known in the art to be safe for human consumption may be used, but powders and particulate substances are preferred because they are easily absorbed by the mouth.

To this point, the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An orally ingested energy supplement, comprising: a small container forming a sealed enclosure with a hollow inner cavity and sized to fit within a human mouth, wherein said small container is constructed of a rapidly dissolving water-soluble film; an energy-enhancing substance enclosed within said inner cavity of said small container; wherein said energy-enhancing substance consisting of caffeine, a sweetener, one or more vitamins, and one or more minerals and/or extracts; wherein said one or more vitamins are selected from the group consisting of vitamin C, thiamine, vitamin B3, vitamin B6, vitamin B12, vitamin A, vitamin E, and minerals and/or extracts are selected from the group consisting of ginkgo biloba, ginger, ginseng, and taurine.

2. The energy supplement of claim 1, wherein said small container has an hourglass shape, with a first end and a second end; wherein said portion of said small container formed of water-soluble film is said first end of said small container.

3. The energy supplement of claim 1, wherein said small container is shaped like a pill sheath, having two halves that engage; wherein said portion of said small container constructed of water-soluble film is one half of said pill sheath.

4. The energy supplement of claim 1, wherein the energy-enhancing substance is a powder.

5. An orally ingested energy supplement, comprising:
   a small container forming a sealed enclosure with a hollow inner cavity and sized to fit within a human mouth, wherein said small container is constructed of a rapidly dissolving water-soluble film;
   an energy-enhancing substance enclosed within said inner cavity of said small container;
   wherein said energy-enhancing substance consisting of caffeine, a sweetener, and one or more vitamins, minerals, and extracts;
   wherein said one or more vitamins, minerals, and extracts are selected from the group consisting of vitamin C, vitamin B3, vitamin B6, vitamin B12, vitamin A, vitamin E, thiamine, ginkgo biloba, ginger, ginseng, and taurine.

6. The energy supplement of claim 5, wherein said energy-enhancing substance is a powder.

* * * * *